United States Patent [19]

Togawa

[11] Patent Number: 5,348,883
[45] Date of Patent: Sep. 20, 1994

[54] SELECTING DEVICE FOR CELLS AND THE LIKE

[75] Inventor: Yoshiyuki Togawa, Osaka, Japan

[73] Assignee: Shimadzu Corporation, Kyoto, Japan

[21] Appl. No.: 968,530

[22] Filed: Oct. 29, 1992

[30] Foreign Application Priority Data

Oct. 30, 1991 [JP] Japan .................. 3-313955

[51] Int. Cl.⁵ .................. C12M 1/34; C12M 1/26
[52] U.S. Cl. .................. 435/291; 435/292;
435/293; 435/30; 73/864.22; 73/864.71;
73/863.21
[58] Field of Search .................. 435/29, 30, 34, 284,
435/285, 287, 291, 292, 293, 297, 298, 299–301,
310, 311, 808, 289; 73/863, 863.01, 863.21,
863.23, 864, 864.11, 864.01, 864.22, 864.15,
864.71, 864.73; 250/222.2, 301, 461.1, 461.2,
462.1; 356/36, 38, 335, 336–338, 244;
422/82.05, 82.08, 82.09, 99–102, 104; 209/45,
49; 414/755

[56] References Cited

U.S. PATENT DOCUMENTS

| | | | |
|---|---|---|---|
| 3,853,711 | 12/1974 | Heden | 435/291 |
| 4,237,223 | 12/1980 | Metz | 435/30 |
| 4,281,066 | 7/1981 | Thran et al. | 435/292 |
| 4,613,573 | 9/1988 | Shibayama et al. | 435/292 |
| 5,073,495 | 12/1991 | Anderson | 435/284 |

FOREIGN PATENT DOCUMENTS

| | | |
|---|---|---|
| 1020068 | 11/1977 | Canada . |
| 0094193 | 11/1983 | European Pat. Off. . |
| 0101572 | 2/1984 | European Pat. Off. . |
| 0168238 | 1/1986 | European Pat. Off. . |
| 0347579 | 12/1989 | European Pat. Off. . |
| 2853596 | 6/1980 | Fed. Rep. of Germany . |
| 0240908 | 11/1986 | Fed. Rep. of Germany ........ 435/30 |
| 9078680 | 5/1984 | Japan ............... 435/292 |
| 1001378 | 1/1986 | Japan ............... 435/292 |
| 1115481 | 6/1986 | Japan . |
| 1115482 | 6/1986 | Japan . |
| 2065700 | 3/1987 | Japan ............... 435/30 |
| 3052871 | 3/1988 | Japan ............... 435/292 |
| 2307164 | 12/1990 | Japan . |
| 3240482 | 10/1991 | Japan ............... 435/292 |
| 8706955 | 11/1987 | PCT Int'l Appl. ............... 435/292 |
| 8908834 | 9/1989 | PCT Int'l Appl. . |
| 1017725 | 5/1983 | U.S.S.R. ............... 435/292 |
| 1537265 | 1/1990 | U.S.S.R. ............... 435/297 |
| 91/05253 | 4/1991 | World Int. Prop. O. . |

Primary Examiner—William H. Beisner
Attorney, Agent, or Firm—Mason, Fenwick & Lawrence

[57] ABSTRACT

Cells and the like, such as granular cells, granular microorganisms and gel beads which embrace cells or microorganisms, are arranged on a support member in a single layer. A detector detects each optical property of the cells and the like, and detectors detect each position of the cells and the like with respect to the structure. Data obtained by the detectors are stored in a memory device. According to the stored data, a control device moves a pickup member relatively in the three dimensional directions with respect to the support member. The pickup member picks up any of the cells and the like which has a specific optical property via an adhesive. Each of the specific cells and the like which adheres to the pickup member is releasable from the pickup member.

5 Claims, 4 Drawing Sheets

Fig. 2
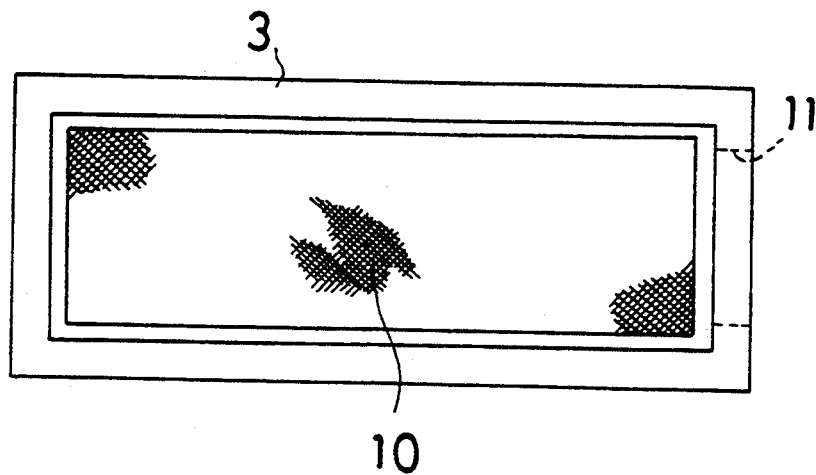
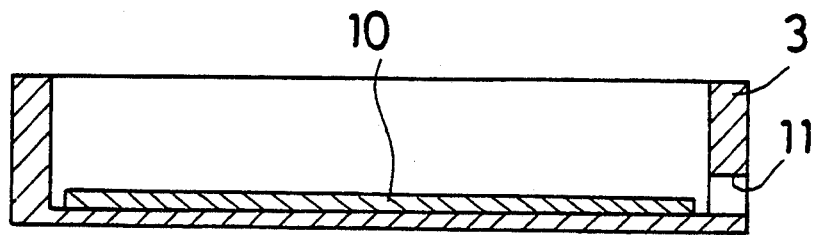
Fig. 3
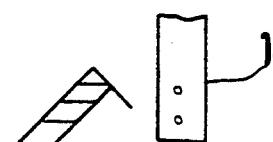
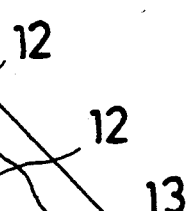
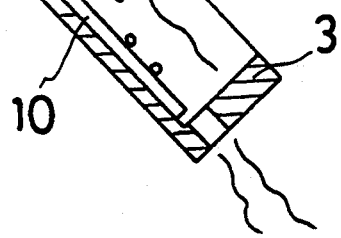
Fig. 4

SELECTING DEVICE FOR CELLS AND THE LIKE

FIELD OF THE INVENTION

The present invention relates to a selecting device suitable for selecting cells and the like. Each of the cells and the like is, for example, cells clumped like a granule, microorganisms clumped like a granule and a gel bead which embraces cells or microorganisms by a carrier such as alginic acid, chitin or agar-agar.

DESCRIPTION OF THE RELATED ART

For example, in a process of forming a hybridoma which produces monoclonal antibodies, many droplets are formed from a culture medium such as alginic acid which embraces cells. The droplets are dropped into calcium chloride solution to form many gel beads. The cells are cultured in the gel beads, and then any of the gel beads which embrace cells producing monoclonal antibodies are selected from among all gel beads.

Since the ratio of the gel beads which embrace cells producing monoclonal antibodies to all gel beads is as low as 1%, it is demanded to select the specific gel beads in an automatic, rapid and reliable manner.

In case of getting microorganisms having specific property, since gel beads which embrace microorganisms are formed by the similar process as above, it is also demanded to select the specific gel beads from among all gel beads in the same way.

In case cells or microorganisms are cultured in a normal culture medium unlike gel beads, they are usually clumped and formed into many granules. Thus, it is demanded to select the specific granular cells or granular microorganisms from among all granular cells or granular microorganisms in the same way.

The objective cells and the like are identified by an optical property of cells themselves, an optical property of microorganisms themselves or an optical property of substance which was secreted from cells or microorganisms. For example, by adding a fluorescent agent combined with a substance which can combine with monoclonal antibodies to the culture medium, luminous granular cells producing monoclonal antibodies or gel beads which embrace luminous cells producing monoclonal antibodies can be identified under dark field of a microscope. Also, granular microorganisms having a specific color or gel beads of which color changes by multiplication of microorganisms embraced in them can be identified under light field of a microscope.

After above identification step, the identified cells and the like are picked up by a needle piercing them or are sucked by a glass tube in a liquid.

In the past, above selecting process is performed almost manually, and thus it is a time consuming and labor intensive operation.

Besides, a gel bead is a minute sphere of which diameter usually ranges from about 0.1 mm to 5 mm, and cells clumped like a granule or microorganisms clumped like a granule has a shape of substantially sphere of which diameter is smaller than that of gel bead. Thus, in case of piercing the cells and the like by the needle, the cells and the like attempt to slip away from the needle. Namely the piercing operation is difficult. Even if the cells and the like are pierced, they soon fall off the needle.

Besides, in case of sucking objective cells and the like by the glass tube, unnecessary cells and the like adjacent to the objective ones are sucked together.

It is an object of the present invention to provide a selecting device for cells and the like, which can solve the above problems.

SUMMARY OF THE INVENTION

The selecting device for the cells and the like according to the present invention comprises a support member capable of arranging the cells and the like thereon in a single layer, means for detecting each position of the cells and the like with respect to the support member, each position of the cells and the like with respect to the support member being determined by two dimensional coordinates, means for detecting each optical property of the cells and the like arranged on the support member, a memory device for storing data corresponding to the positions and the optical properties of the cells and the like, a pickup member capable of picking up each of the cells and the like arranged on the support member via an adhesive, a driving means for moving the pickup member relatively in the three dimensional directions with respect to the support member, a control device for controlling the driving device in accordance with the stored data so that the pickup member can pick up any of the cells and the like which has a specific optical property, and means for releasing each of the specific cells and the like which adheres to the pickup member from the pickup member.

According to the present invention, by arranging the cells and the like in a single layer on the support member, each position of the cells and the like is fixed on a plane defined by the two dimensional coordinates. Namely, each position of the cells and the like with respect to the support member can be determined by the abscissa and ordinate. And each optical property of the cells and the like arranged on the support member can be correlated to each position of the cells and the like. The data corresponding to the positions and the optical properties of the cells and the like are stored in the memory device. In accordance with the stored data, the control device controls the driving means so that the pickup member moves relatively in the three dimensional directions with respect to the support member. Thereby the pickup member can pick up any of the cells and the like which has a specific optical property via the adhesive. Then, the pickup member is transferred above a container such as a micro well, and each of the specific cells and the like which adheres to the pickup member is released from the pickup member. Therefore, the selecting device according to the present invention can select the specific cells and the like in a rapid and reliable manner, and can contribute to automating of the selecting operation.

Preferably, each of the cells and the like is cells clumped like a granule, microorganisms clumped like a granule or a gel bead embracing cells or microorganisms. Preferably, the support member is a mesh, a structure having plural grooves or a structure having plural dimples. Preferably, the pickup member is a capillary through which a current of gas is blown so that each of the specific cells and the like which adheres to the capillary is released from the capillary.

BRIEF DESCRIPTION OF THE DRAWINGS

FIG. 2 is a plan view showing a transparent container of the embodiment according to the present invention;

FIG. 3 is a cross-sectional view showing a transparent container of the embodiment according to the present invention;

FIG. 4 illustrates the operation of the embodiment according to the present invention;

DETAILED DESCRIPTION OF THE PREFERRED EMBODIMENTS

Figure 1:
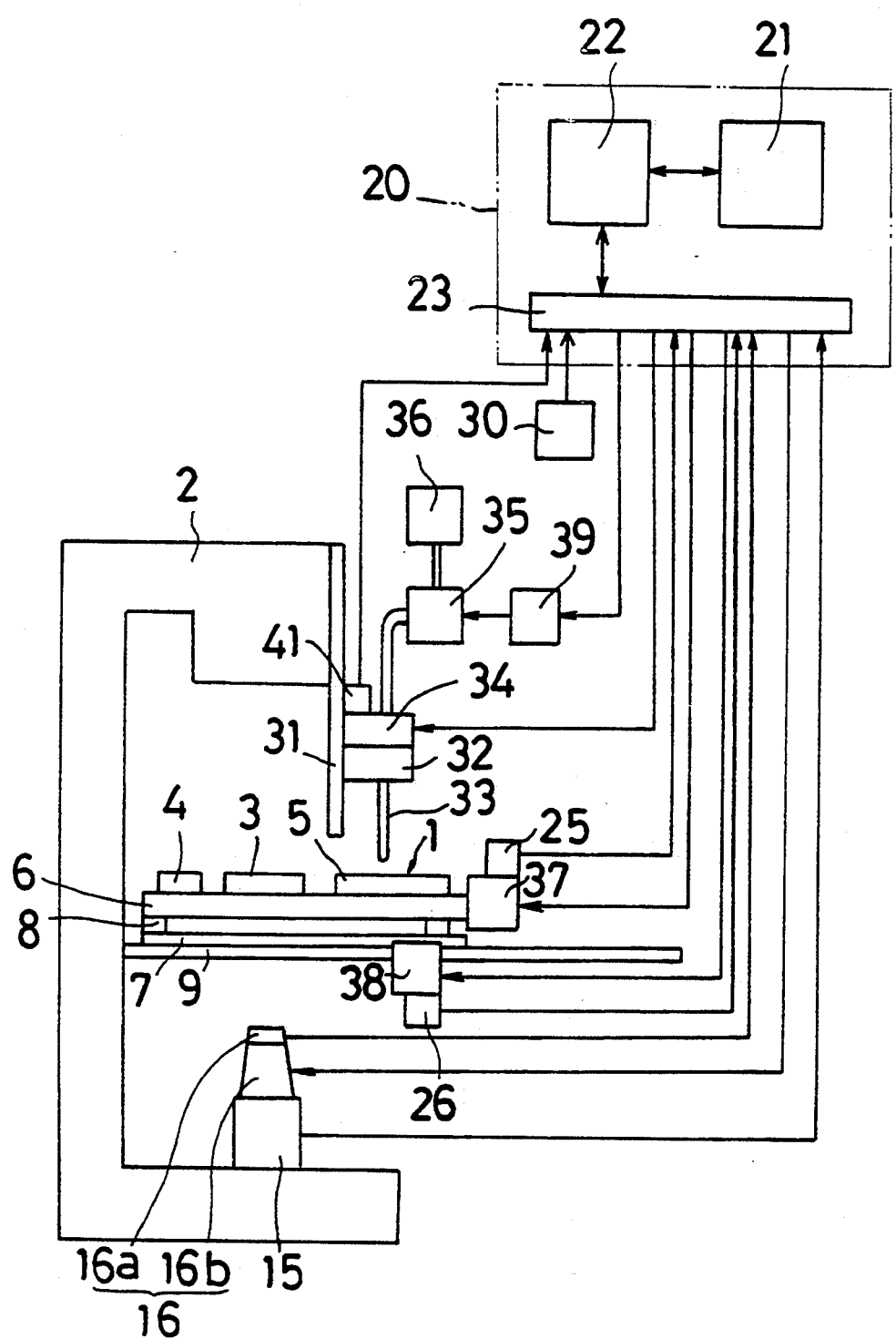
FIG. 1 is a view showing the construction of the selecting device of the embodiment according to the present invention.

Referring to the drawings, the embodiments of the present invention are described.

As shown in FIG. 1, a selecting device 1 is mounted on an optical microscope 2. The selecting device 1 has a first support frame 6 on which a transparent container 3 for containing cells and the like, an container 4 for containing adhesive and a container 5 including plural micro wells are mounted. The first support frame 6 is movable on a rail 8 fitted to a second support frame 7. The rail 8 guides the first frame 6 into a substantially horizontal direction (X-axis direction) perpendicular to the page on which FIG. 1 is drawn. The second support frame 7 is movable on a rail 9 fitted to the microscope 2. The rail 9 guides the second frame 7 into a substantially horizontal direction (Y-axis direction) perpendicular to the X-axis direction.

Figure 5:
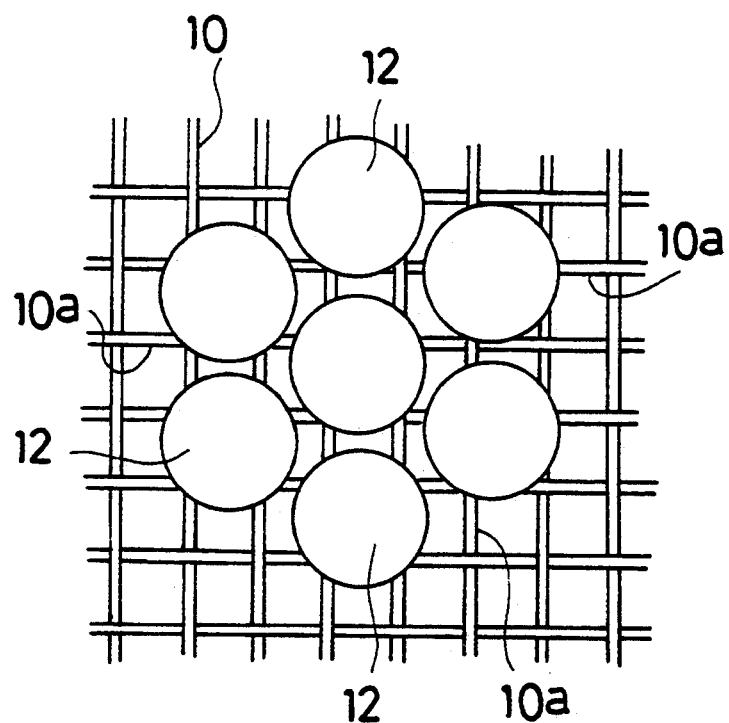
FIG. 5 illustrates the mesh of the embodiment according to the present invention.

As shown in FIG. 2 and FIG. 3, the top end of the transparent container 3 is open. A mesh 10 is mounted on the inner bottom of the container 3 as a support member. A drain hole 11 is provided on the side wall of the container 3. A suspension 13 including cells and the like 12 is introduced into the container 3 tilted from a horizontal plane as shown in FIG. 4 through an inlet duct 14, then the liquid component of the suspension 13 is drained through the drain hole 11. Then the container is mounted on the first support frame 6. Thus the cells and the like 12 are arranged on the mesh 10 along the X-axis and Y-axis. As shown in FIG. 5, the size of each opening 10a of the mesh 10 is set smaller than the size of each of the cells and the like 12 so that the cells and the like 12 are arranged in a single layer. As long as the cells and the like 12 are arranged, the size of each opening 10a may be slightly greater than the size of each of the cells and the like 12. In case each of the cells and the like 12 is a gel bead which embraces cells or microorganisms, each diameter of the gel beads usually ranges from about 0.1 mm to 5 mm. In case each of the cells and the like 12 is cells clumped like a granule or microorganisms clumped like a granule, each diameter of them is smaller than the diameter of a normal gel bead. Therefore the size of each opening 10a is determined depending on the diameters of the cells and the like 12. Preferably, the atmosphere surrounding the container 3 is a humidified one in order to enhance the survival rate of cells and microorganisms.

Any of the cells and the like 12 have a specific optical property based on their own property or based on substance secreted from them. For example, by adding a fluorescent agent combined with a substance which can combine with monoclonal antibodies to a culture medium for the cells, granular cells producing monoclonal antibodies or gel beads which embrace cells producing monoclonal antibodies emit fluorescence under the dark field. In case granular cells or granular microorganisms have a specific color, by lighting the cells and the like 12, the reflective rate of the light of which wavelength agrees with the specific color increases. In case cells or microorganisms are achromatic, the lightness of the gel beads 12 which embrace the cells or microorganisms changes by multiplication of cells or microorganisms under the light field.

To detect each optical property of the cells and the like 12, an image pickup device 15 having an image sensor and a lens system is disposed below the container 3. An automatic focusing device 16 which is used to focus the image of each of the cells and the like 12 on the image pickup device 15 is provided. The automatic focusing device 16 is useful in case each diameter of the cells and the like 12 or the thickness of the mesh 10 is not uniform. The automatic focusing device 16 has a distance sensor 16a measuring the distance to each of the cells and the like 12 and a moving device 16b moving the lens system. The distance sensor 16a and the moving device 16b are connected to a microcomputer (controller) 20 which is described later. The microcomputer 20 generates a signal according to the distance measured by the distance sensor 16a, and the moving device 16b moves the lens system according to the signal from the microcomputer 20 to focus the image of each of the cells and the like 12 on the image pickup device 15. In case each of the cells and the like 12 has an optical property of fluorescence, image data corresponding to the intensity of the fluorescence are obtained by picking up the image of each of the cells and the like 12 under the dark field. In case each of the cells and the like 12 has a specific color or a specific lightness, image data corresponding to the color or the lightness are obtained by picking up the image of each of the cells and the like 12 under the light field.

Each optical property of the cells and the like 12 is stored in a memory device 21 of the microcomputer 20. To be more precise, the microcomputer 20 comprises the memory device 21, a central processor unit 22 and an input/output interface unit 23. The image pickup device 15 is connected to the input/output interface unit 23 via an analog-to-digital (A-D) converter which digitizes the image data corresponding to the optical properties of the cells and the like 12. The memory device 21 has memory areas. Each position of the cells and the like 12 with respect to the mesh 10 can be correlated to any of the memory areas. Each position of the cells and the like 12 with respect to the mesh 10 is determined by the abscissa and ordinate. Each coordinates of the cells and the like 12 are detected by sensors 25, 26 as described later, and the coordinate data are input to the microcomputer 20. Thereby the digitized image data of the cells and the like 12 are stored in the memory areas corresponding to the coordinates of the cells and the like 12.

A support member 32 is fitted to the microscope 2 via a rail 31. The rail 31 guides the support member 32 into a substantially vertical direction (Z-axis direction) perpendicular to the X-axis and Y-axis directions. The support member 32 supports a capillary (pickup member) 33 which is connected to a high-pressure air source 36 via an electromagnetic valve 35. A driving device 39 of the electromagnetic valve 35 is connected to the microcomputer 20. The capillary 33 is movable relatively along the X-axis, Y-axis and Z-axis with respect to the mesh 10. Thus, the capillary 33 can contact a adhesive 40 inside the container 4, and can pick up each of the cells and the like 12 arranged on the mesh 10 via the adhesive 40, and can be located above any of micro wells inside the container 5. As the adhesive 40 a viscous material which is physiologically less toxic, such as starch adhesive, is preferred.

Driving means are provided to move the capillary 33 relatively along the X-axis, Y-axis and Z-axis directions with respect to the mesh 10. To be more precise, the driving means have a driving device 37 for moving the first support frame 6 in the X-axis direction with respect to the rail 8, a driving device 38 for moving the second support frame 7 in the Y-axis direction with respect to the rail 9 and a driving device 34 for moving the support member 32 in the Z-axis direction with respect to the rail 31. For example, each of the driving devices 34, 37, 38 may have a rack, a pinion meshed with the rack, a motor for driving the pinion and a driving circuit for the motor, whereby each rack may be fitted to the rails 8, 9, 31 and the motor may be fitted to the movable members 6, 7, 32. In case each of the cells and the like 12 is cells clumped like a minute granule or microorganisms clumped like a minute granule, it is desirable to adopt a piezoelectric actuator having a high resolution positioning capability as the driving devices 34, 37, 38. The piezoelectric actuator may have piezoelectric elements fitted to the rails 8, 9, 31, and the movable members 6, 7, 32 may be moved in response to the displacements of the piezoelectric elements. Each driving device 34, 37, 38 is connected to the microcomputer 20 so as to be controlled by the microcomputer 20.

A sensor 25 for measuring the travel of the first support frame 6 in the X-axis direction with respect to the first rail 8, a sensor 26 for measuring the travel of the second support frame 7 in the Y-axis direction with respect to the second rail 9 and a sensor 41 for measuring the travel of the support member 32 in the Z-axis direction with respect to the rail 31 are provided. Each of the sensors 25, 26, 41, for example, may measure the travel by detecting the number of revolutions of each pinion of the driving devices 34, 37, 38. Each of the sensors 25, 26, 41 may measure the travel by detecting the fluctuations of the electric field acting on the piezoelectric elements of the driving devices 34, 37, 38. The sensors 25, 26 are respectively connected to the microcomputer 20 so that each abscissa and each ordinate of the cells and the like 12 arranged on the mesh 10 can be determined by the signals fed from the sensor 25, 26. The sensor 41 is connected to the microcomputer so that the coordinate of the capillary 33 with respect to the cells and the like 12 along the Z-axis can be determined by the signal fed from the sensor 41. The origin of the X-axis, Y-axis and Z-axis may be set anywhere on the mesh 10.

The selecting device 1 constructed as above is controlled by the microcomputer 20 as below according to the sequence of the control program stored in the memory device 21.

In the first place, one of the cells and the like 12 arranged on the mesh 10 is picked up by the image pickup device 15 to detect the optical property of it 12 via the automatic focusing device 16. The abscissa and the ordinate of it 12 are determined by the signals fed from the sensors 25, 26. The image data in accordance with the optical property of it 12 are fed to the memory device 21 and stored in the memory area corresponding to the coordinates of it 12.

In the next place, by the movements of the support frames 6, 7, another one of the cells and the like 12 is positioned on the focal point of the image pickup device 15, and the same process as above is repeated.

By the repetition of above process, the optical data corresponding to the properties of all of the cells and the like 12 arranged on the mesh 10 are stored in the memory device 21 together with the coordinate data corresponding to the coordinates of all of them 12.

Figure 6:
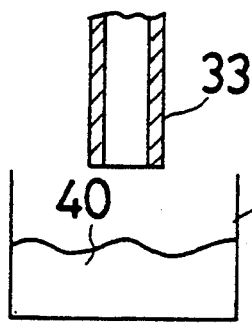
FIG. 6(i) to FIG. 6(g) illustrate the operation of the embodiment according to the present invention.
Figure 6:
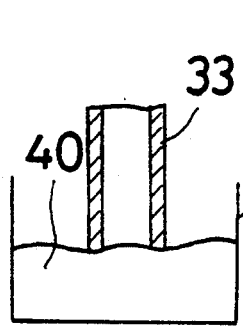
Figure 6:
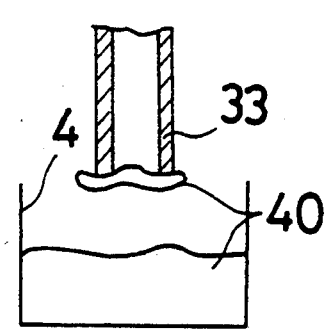
Figure 6:
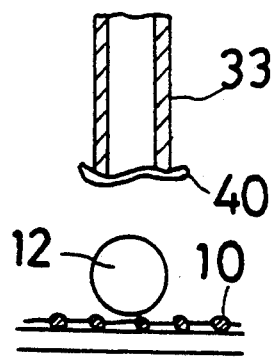
Figure 6:
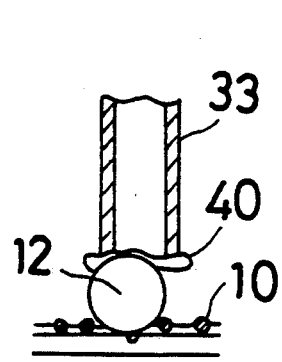
Figure 6:
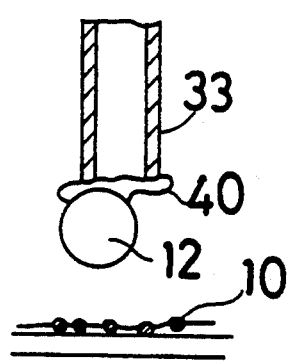
Figure 6:
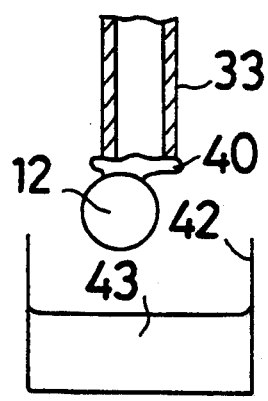
Figure 6:
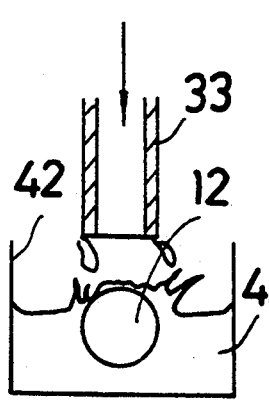
Figure 6:
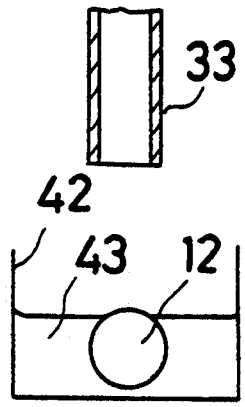

In the next place, the support frames 6, 7 are moved so that the adhesive container 4 is located below the capillary 33 as shown in FIG. 6(1), and then, the support member 32 is moved so that the adhesive 40 sticks to the bottom end of the capillary 33 as shown in FIG. 6(2), FIG. 6(3). Then the support frames 6, 7 are moved so that the capillary 33 is located above one of the cells and the like 12 which has a specific optical property as shown in FIG. 6(4). For example, in case the cells and the like 12 emit fluorescence, the capillary 33 is located above any of the cells and the like 12 of which intensity of the fluorescence is beyond a certain threshold level. Then the support member 32 is moved so that the capillary 32 picks up the one of the cells and the like 12 via the adhesive 40 as shown in FIG. 6(5), FIG. 6(6). Then the support frames 6, 7 are moved so that one of the micro wells 42 in the container 5 is located under the capillary 33 as shown in FIG. 6(7). Then a signal for opening the valve 35 is fed to the driving device 39 so that a current of compressed air is blown through the capillary 33 (illustrated by the arrow in FIG. 6(8)). Thereby, the one of the cells and the like 12 which adheres to the capillary 33 is released, and it 12 is received by the micro well 42 as shown in FIG. 6(9). The micro well 42 contain a buffer solution 43. In case the pressure of the compressed air blown through the capillary 33 is not so high or in case each of the cell and the like 12 is gel bead of which hardness is high, the buffer solution 43 is not necessary. By repeating the above process illustrated by FIG. 6(1)~(9), any of cells and the like 12 which have the objective optical property are respectively received by the micro wells 42.

By the above process, cells or microorganisms having a specific useful substance can be obtained.

Figure 7:
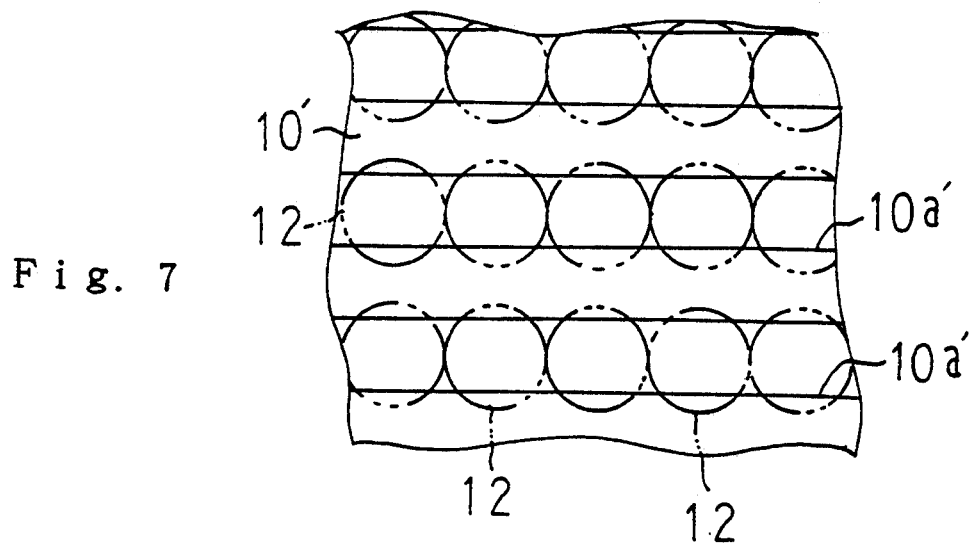
FIG. 7 illustrates a modified support member.
Figure 8:
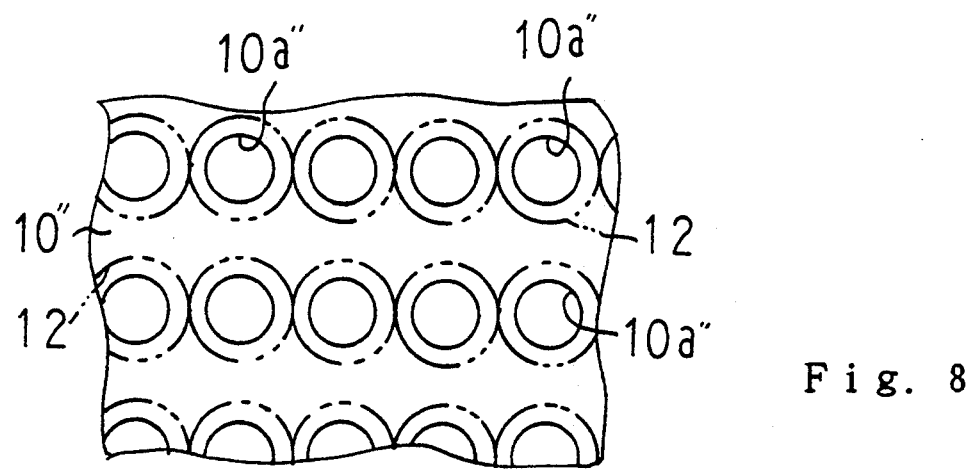
FIG. 8 illustrates another modified support member.

The present invention is not limited to the above embodiment. For example, while in the above embodiment the support member is a mesh 10, alternatively, a support member may be a structure 10' having plural grooves 10a' on which the cells and the like 12 are arranged as shown in FIG. 7. Alternatively, a support member may be a structure 10" having plural dimples 10a" on which the cells and the like 12 are arranged as shown in FIG. 8. As an alternative to the use of the image pickup device 15, a manual operation switch 30 connected to the interface unit 23 may be used. To be more precise, when an operator who observes the cells and the like 12 via the microscope 2 recognizes an objective optical property, the operator inputs a sensing signal to the microcomputer 20 by means of the switch 30. The sensing signal is stored as data corresponding to the objective optical property in the memory area corresponding to the coordinates of the recognized one of the cells and the like 12. Further, when any abnormal one of the cells and the like 12 is found via the microscope 2, it 12 may be picked up separately or may not be picked up by feeding a signal to the microcomputer 20 by means of the switch 30. The mesh 10 may be formed on a wafer using the semiconductor patterning technique. As an alternative to compressed air, another type of gas may be blown through the capillary 33. While in the above embodiment the liquid component of the solution 13 is drained by tilting the transparent container 3 as shown in FIG. 4, alternatively, the solution 13 may be drained by sucking it through the capillary 33.

What is claimed is:

1. A device for selecting cells, microorganisms, or gel beads comprising: a support member capable of arranging cells, microorganisms, or gel beads thereon;

means for detecting a specified optical property of cells, microorganisms, or gel beads on said support member and identifying the position of cells microorganisms or gel beads possessing such optical property by means of two-dimensional coordinates relative to the support member;

a memory device for storing the two-dimensional coordinates of the cells, microorganisms, or gel beads to be selected;

an adhesive in a container;

a capillary pickup member;

a driving means for moving a bottom end of the capillary pickup member into contact with said adhesive, and further capable of moving said capillary pickup member three-dimensionally relative to the support member;

a control device for controlling the driving means in accordance with said stored coordinates so that the adhesive on the bottom end of the capillary pickup member picks up the cells, microorganisms, or gel beads having the specified optical property; and said capillary pickup member is connected to a pressurized gas source such that gas is blown through the capillary pickup member to release the cells, microorganisms., or gel beads adhering to the bottom end of the capillary pickup member.

2. The selecting device of claim 1 wherein said pickup member is capable of picking up said cells, microorganisms, or gel beads when they are clumped together like a granule.

3. The selecting device according to claim 1, wherein the support member is a mesh.

4. The selecting device according to claim 1, wherein the support member is a structure having plural grooves.

5. The selecting device according to claim 1, wherein the support member is a structure having plural dimples.

* * * * *